(12) United States Patent  
Feiweier et al.

(10) Patent No.: US 9,952,303 B2
(45) Date of Patent: Apr. 24, 2018

(54) METHOD FOR AUTOMATIC CALIBRATION OF MOTION DETECTION TECHNIQUES IN MEDICAL IMAGING SYSTEMS

(71) Applicant: SIEMENS HEALTHCARE GMBH, Erlangen (DE)

(72) Inventors: Thorsten Feiweier, Poxdorf (DE); Tobias Kober, Lausanne (CH); Gunnar Krueger, Watertown-Boston, MA (US)

(73) Assignee: Siemens Aktiengesellschaft, Munich (DE)

( * ) Notice: Subject to any disclaimer, the term of this patent is extended or adjusted under 35 U.S.C. 154(b) by 510 days.

(21) Appl. No.: 14/639,302

(22) Filed: Mar. 5, 2015

(65) Prior Publication Data

US 2015/0253409 A1 Sep. 10, 2015

(30) Foreign Application Priority Data

Mar. 5, 2014 (EP) .................................... 14157778

(51) Int. Cl.
*G01R 33/30* (2006.01)
*G01R 33/567* (2006.01)
(Continued)

(52) U.S. Cl.
CPC ............ *G01R 33/5673* (2013.01); *A61B 5/11* (2013.01); *A61B 5/7207* (2013.01); *G01P 21/00* (2013.01);
(Continued)

(58) Field of Classification Search
None
See application file for complete search history.

(56) References Cited

U.S. PATENT DOCUMENTS

| 5,930,741 A | 7/1999 | Kramer |
| 7,216,053 B2 | 5/2007 | Rakkola et al. |
| (Continued) | | |

FOREIGN PATENT DOCUMENTS

| DE | 102006055933 B4 | 4/2010 |
| WO | 2006070272 A2 | 7/2006 |
| WO | 2007136745 A2 | 11/2007 |

OTHER PUBLICATIONS

Kober, T., Gruetter, R., Krueger, G., Prospective and retrospective motion correction in diffusion magnetic resonance imaging of the human brain (2012). NeuroImage, 59(1), 389-398, ISSN 1053-8119.*

(Continued)

*Primary Examiner* — Charles Garber
*Assistant Examiner* — Alia Sabur
(74) *Attorney, Agent, or Firm* — Laurence Greenberg; Werner Stemer; Ralph Locher

(57) ABSTRACT

A motion detection system detects object motion in a medical imaging system. The computer-implemented calibration method includes an automatic calibration process for determining a motion threshold for the object motion detection system, while the object is positioned for imaging by the medical imaging system. The calibration process includes: repeatedly acquiring motion detection data and repeatedly acquiring motion quantification data with a motion quantification system. The motion quantification data are analyzed to determine whether the object was mobile or immobile. If the object was immobile, an object motion threshold for the motion detection system is determined by statistical analysis of the motion detection data. If the object was mobile, the detection and quantification data are correlated for determining an object motion threshold for the motion detection system, the threshold being determined from motion detec- (Continued)

tion data correlated to motion quantification data characterizing an object motion within a predefined tolerance value.

13 Claims, 1 Drawing Sheet

(51) Int. Cl.
A61B 5/00 (2006.01)
A61B 5/11 (2006.01)
G01R 33/563 (2006.01)
G01R 33/565 (2006.01)
G01R 33/56 (2006.01)
G01P 21/00 (2006.01)
G01R 33/561 (2006.01)

(52) U.S. Cl.
CPC ....... *G01R 33/307* (2013.01); *G01R 33/5608* (2013.01); *G01R 33/56308* (2013.01); *G01R 33/56509* (2013.01); *A61B 5/721* (2013.01); *G01R 33/5616* (2013.01); *G01R 33/5676* (2013.01)

(56) References Cited

U.S. PATENT DOCUMENTS

| 7,561,909 | B1 | 7/2009 | Pai et al. |
| 8,571,293 | B2 | 10/2013 | Ernst et al. |
| 2008/0214923 | A1 | 9/2008 | Krueger et al. |
| 2011/0080167 | A1 | 4/2011 | Kannengisser et al. |
| 2013/0121367 | A1 | 5/2013 | Ahuja et al. |

OTHER PUBLICATIONS

Herbst, M., Maclaren, J., Weigel, M., Korvink, J., Hennig, J. and Zaitsev, M. (2012), Prospective motion correction with continuous gradient updates in diffusion weighted imaging. Magn. Reson. Med., 67: 326-338. doi:10.1002/mrm.23230.*

Maclaren, J., Speck, O., Stucht, D., Schulze, P., Hennig, J. and Zaitsev, M. (2010), Navigator accuracy requirements for prospective motion correction. Magn. Reson. Med., 63: 162-170. doi:10.1002/mrm.22191.*

Kober, T., Marques, J. P., Gruetter, R. and Krueger, G. (2011), Head motion detection using FID navigators. Magn. Reson. Med., 66: 135-143. doi:10.1002/mrm.22797.*

Maclaren, J., Herbst, M., Speck, O. and Zaitsev, M. (2013), Prospective motion correction in brain imaging: A review. Magn Reson Med, 69: 621-636. doi:10.1002/mrm.24314.*

Babayeva, M., Loktyushin, A., Falkovskiy, P., Kober, T., Mueli, R., Gruetter, R., Krueger, G. (2014). FID navigator triggered acquisition of imaging navigators for retrospective head motion correction. ISMRM Workshop on Motion Correction, Jul. 2014.*

Waszak, M. V. (2016); Motion Correction in Magnetic Resonance Imaging Using the Signal of Free-Induction-Decay. Thesis 6963, EPFL.*

Dyverfeldt, P., Deshpande, V. S., Kober, T., Krueger, G., & Saloner, D. (2014). Reduction of Motion Artifacts in Carotid MRI using FID Navigators. Journal of Magnetic Resonance Imaging : JMRI, 40(1), 214-220.*

Kober, T., et al. "Prospective and retrospective motion correction in diffusion magnetic resonance imaging of the human brain," NeuroImage, Academis Press, Orlando, FL., vol. 59, pp. 389-398; ISSN: 1053-8119; DOI: 10 1016/J NeuroImage Jul. 4, 2011; XP02832709; 2012; Jul. 4, 2011.

Dyverfelt P., et al., "Motion compensated carotid MRI using FID navigators," Journal of Cardiovascular Magnetic Resonance, Biomed Central Ltd. London, vol. 15; Suppl. 1; pp. P242 1-3; ISSN: 1532-429X; DOI: 101186/1532-429X-15-S1-P242; XP021136662; 2013; GB; Jan. 30, 2013.

\* cited by examiner

METHOD FOR AUTOMATIC CALIBRATION OF MOTION DETECTION TECHNIQUES IN MEDICAL IMAGING SYSTEMS

CROSS-REFERENCE TO RELATED APPLICATION

This application claims the priority, under 35 U.S.C. § 119, of European patent application EP 14157778.3, filed Mar. 5, 2014; the prior application is herewith incorporated by reference in its entirety.

BACKGROUND OF THE INVENTION

Field of the Invention

The invention relates generally to biomedical imaging, and more specifically to a method for automatically calibrating motion detection resulting from patient motion and occurring during medical imaging, for example during Magnetic Resonance Imaging (MRI).

While the present invention might be applicable to any medical imaging technique, such as MRI, Positron Emission Tomography (PET), or Computed Tomography (CT), and is therefore not specific to a single medical imaging technique, the example of MRI will be taken as main illustration of the present invention. For obtaining images by way of MRI, a subject/object has to be placed in a strong static magnetic field, which forces the hydrogen nuclear magnetic moments associated with the subject/object hydrogen nuclear spins to adopt an orientation parallel or anti-parallel with respect to said static magnetic field giving rise to a net magnetization in the direction of the static magnetic field. In order to stimulate a signal from the hydrogen nuclei, a radiofrequency (RF) excitation pulse can be applied to the subject at a characteristic frequency, the so-called Larmor frequency, which is for one type of nuclei proportional to the flux density of the magnetic field. The transversal magnetic field associated with this excitation pulse disturbs the net magnetization from its equilibrium, rotating it away from the static magnetic field with an angle, called flip angle, which depends on the strength and duration of the magnetic component of the electromagnetic radio frequency radiation. Consequently, the net magnetization begins to precess around the static magnetic field main axis with the Larmor frequency, its transverse component inducing an electromotive force in a receiver coil according to Faraday's law of magnetic induction.

This electromotive force gives rise to an induced signal that is emitted from the subject in response to the RF excitation pulse and magnetic field gradients applied to the subject. The induced signals, hereafter MRI readout signals or simply readouts, form the basis of MR image reconstruction. The magnitude of the MRI readout signal depends, among other factors, on the number of nuclei that produce the magnetization and on their relaxation times, e.g., the characteristic time needed by the net magnetization to return to its equilibrium state along the axis of said strong magnetic field (called longitudinal or T1-relaxation) or the time that characterizes the loss of signal coherence (called transversal or T2-relaxation). Other factors include the so called spin preparation. Indeed, in order to optimize a diagnostic value of the signal, different MRI pulse sequences combining one or more RF pulses might be used, wherein parameters such as the repetition time of the pulse sequence, its echo time, the flip angle, its bandwidth, might be tuned and adapted in function of the parts/functions of the subject that have to be imaged.

Usually, the MRI spatial encoding is done in the three dimensions. One dimension (e.g. along the z direction) is typically determined by slice/slab-selective excitation, and the other two dimensions are usually determined respectively by applying a magnetic field gradient across the excited slice (along a readout direction, e.g. along the x direction), and by applying a brief gradient pulse before each line of the MRI readout signal on one (2D imaging, along a first phase encoding direction, e.g. along the y direction) or two (3D imaging, along a second phase-encoding direction, e.g. along z) gradient axes. The k-space or k-space matrix, i.e. the representation in the spatial-frequency domain of the MRI raw data provided by the MRI readout signal before it has been Fourier-transformed in order to make the final image of the object of interest, is usually represented as a matrix in two or three dimensions in which digitized MRI readout signals are stored during data acquisition. Usually, an Analog to Digital Converter is used for the conversion of the analog signal resulting from the subject/object excitation to a series of digital values, i.e. said digitized MRI readouts, by measurements performed at different times T. Each readout is basically a group of k-space sample points. When the k-space is fully or sufficiently sampled, the k-space data are processed to produce said final image. In conventional MRI, regular k-space traversal patterns are used: the k-space is, for example, completed line by line by acquiring the data samples from the MRI readout signal.

One of the major problems often faced in the field of medical imaging, and in particular in MRI, is subject motion during data acquisition. The presence of motion usually results in image artifacts which can cause major problems in several post-processing procedures and can, in more extreme cases, even affect the diagnostic information. The problem of subject/patient motion during data acquisition time concerns especially children, elderly patients or patients in pain who cannot remain still for the entire duration of the measurement. Patient motion during data acquisition may thus impact the image quality so that a new data acquisition becomes necessary, sometimes requiring also patient sedation. Patient motion thus increases consequently the time needed for performing data acquisition, and of course, the costs of the medical examination. Furthermore, patient comfort is also impeded.

While patient motion occurring exclusively between two image acquisitions can be corrected by means of methods based on pre-registered data/images, patient motion occurring during an image acquisition generally leads to said artifacts. The patient motion can take various forms, like for example rigid body motion of the head or a joint, periodic cardiac or respiratory motion, or deformations (in organs, e.g. peristalsis). Once the motion is detected and/or quantified, it is possible to mitigate artifacts and thus improve the resulting image quality. Therefore, several image data acquisition methods are based on a detection or tracking of motion of the patient body or parts of the patient body for improving the final images. For example, it is possible to track the motion of a patient body and to trigger the acquisition of data based on said tracking (such a technique is notably used for periodic movements, e.g. respiration), or to adapt the acquisition parameters according to said tracking in order to compensate for the motion (notably used in the case of rigid body motion), or to correct the obtained image by means of motion information deduced from said tracking, or to proceed to a new acquisition of data (re-acquisition) only for readouts wherein a motion has been detected by means of the tracking. In any case, the availability of a rapid, robust, reliable and precise method for detecting or quantifying the motion of the patient body is decisive for improving the image quality of the known medical imaging techniques. The goal of motion correction techniques is for example to react to the occurrence of motion either by adapting the acquisition parameters during scan time as soon as motion is detected (prospective motion correction) or correcting the acquired motion-corrupted data before/during/after reconstruction (retrospective motion correction).

In the particular case of MRI, various methods for improving the MRI quality are already known from the skilled man and often only work with dedicated devices. They are for example the respiration belt method for detecting and measuring the respiration motion during an MRI scan, pulse measurement methods that might detect heart motion, electrocardiogram methods, or also camera systems used for quantifying the motion. Furthermore, the abovementioned methods have generally to be combined or to cooperate with special acquisition techniques or with motion deduction techniques in order to allow an improvement of the final images. Examples of such techniques are the Pencil-Beam-Navigators, the FID-Navigators (Free Induction Decay Navigators), the k-Space-Navigators, or the re-acquisition of specific volume data-sets after analyzing time series data.

Unfortunately, the precision of motion detection and the speed at which the motion is detected exclude themselves mutually. Indeed when a motion is rapidly detected, it generally does not provide any quantitative information about the motion, and the precise quantification of said motion requires then an additional procedure that is time consuming. For example, the motion detection by way of a FID-Navigator or a respiration belt takes about 1 millisecond or less, while the quantification of the motion, for example, by means of a camera system or by means of volume dataset analysis requires respectively 10 milliseconds and a few hundred milliseconds.

In order to reduce the time needed for acquiring improved images, it has been suggested to combine both motion detection and motion quantification methods (see for instance NeuroImage 59:389 (2012)): during the diagnostic measurements, a very fast motion detection is rapidly and repeatedly executed, and a precise motion quantification is then done only when a significant movement (i.e. above a predefined motion threshold) has been detected. By this way the advantages of both motion detection and quantification methods are combined for improving the final images. Nevertheless, one difficulty that remains is the determination of the motion threshold that characterizes a significant movement. Indeed, there is no a-priori linear dependence between the patient motion (amplitude and direction) and its impact on the acquired data. In fact, the motion threshold depends mainly on the patient himself and on the configuration of the medical imaging system used during the medical diagnosis.

Some techniques have been proposed for determining a motion threshold, i.e. for calibrating the motion detection in order to determine when a motion that has occurred has to be corrected or, in other words, from which motion amplitude/direction, acquired data have to be considered as corrupted.

For example, in the case of periodical movements (e.g. breathing, heartbeat) the acquired data also have a corresponding oscillating behavior. By acquiring data over several cycles of said periodical movements and analyzing said data, it is possible to identify some state of motion (e.g. expiration, i.e. short time rest condition) and then to use said identification of motion state for triggering the data. Unfortunately, this technique works only with periodical movements and requires repeated acquisition of data for the determination of said state of motion.

Another technique consists in empirically fixing the motion threshold. Such a technique is described, for example, in commonly assigned published patent application No. US 2008/0214923 A1 and its counterpart German patent DE 10 2006 055 933 B4. It requires the acquisition of data with and without body motion from a set of test persons, wherein the data are acquired within a specific configuration of the MRI system. Then a statistic treatment of the data thus obtained allows the extraction of a motion threshold that will be used for patient motion correction when imaging with said specific configuration. This technique has the disadvantage of requiring a new calibration for each new configuration of the MRI system and may depend on the difference in physiology between the mean physiology of the test persons and the patient.

A further technique requires generating reference displacements of an object relative to an MRI coil, wherein each displacement is spatially and metrically predefined and recording corresponding intensity changes of navigator signals at the coil (see, for example, commonly assigned US 2011/0080167 A1). In this way, it is possible to associate changes of position of the object with changes of the intensity signal and to construct a calibration map that is reversely used to deduce the object motion from measured MRI intensity signals during real patient measurements, as well as to define a motion threshold. Unfortunately, generating reference displacements as a routine in a clinic is not possible since it requires precise displacements respecting a predefined model.

SUMMARY OF THE INVENTION

It is accordingly an object of the invention to provide a method for automatically calibrating motion detection in a medical imaging system that is specifically adapted to clinical routine which overcomes the above-mentioned and other disadvantages of the heretofore-known devices and methods of this general type and which method is capable of automatically determining a threshold that is patient and system configuration specific (i.e. specific to the system as used for imaging the patient). The present invention aims thus to provide a method for calibrating a motion detection technique in clinical routine and automatically determining a motion threshold, working for periodic and for non-periodic motion.

With the foregoing and other objects in view there is provided, in accordance with the invention, a computer-implemented method for calibrating a motion detection system working according to a motion detection technique and configured for detecting a motion of an object during medical imaging, e.g. during an MRI scan, by means of a medical imaging system, e.g. an MRI scanner, the computer-implemented method comprising a calibration process for determining at least one motion threshold for said object motion detection system, said calibration process taking place preferentially before starting a diagnostic measurement or in parallel with a diagnostic scan, and for said object being in a position and place allowing its imaging by said medical imaging system, e.g. placed inside the static magnetic field of the MRI scanner, said object being moreover free to move. The calibration process comprises:

a. using the motion detection system working according to the motion detection technique (such as FID-navigator, or a respiratory belt, or pencil-beam-navigator or a motion detection method monitoring the diagnostic data during acquisition, . . . ) for repeatedly acquiring motion detection data enabling object motion detection (fast detection of motion) and using a motion quantification system working according to a motion quantification technique (such as MR image navigator, camera system, . . . ) for repeatedly acquiring motion quantification data enabling object motion quantification (precise quantification of motion), wherein the motion quantification data are parameters enabling a modeling of the object motion and motion detection data are parameters indicating whether an object motion above a threshold occurred or not. In particular, motion detection data and motion quantification data are simultaneously or alternately acquired. Preferentially, during the calibration process, the acquisition of motion detection data and motion quantification data is configured for providing information about an object motion taking place during a time interval with two sets of data for said time interval, respectively a set of motion quantification data and a set of motion detection data. In other words, a same object motion might be advantageously characterized according to the present invention by said two sets of data taken during the same time interval during which the object motion took place;

b. analyzing the motion quantification data for determining if said object moved or not (i.e. was mobile or immobile), in particular, analyzing the motion quantification data for determining if said object moved during said time interval; and i. if the object was immobile, in particular immobile during said time interval, then using the motion detection data which are in particular acquired simultaneously or alternately to the motion quantification data, and in particular using the set of motion detection data acquired during said time interval, for determining the object motion threshold for the motion detection system wherein said object motion threshold is determined by statistically analyzing the motion detection data. Advantageously, since the object is immobile, all motion detection data are taken for an identical position of the object, and are thus directly workable to determine said object motion threshold by means of statistical analysis. In particular, the object motion threshold is determined by calculating a mean value m and/or a standard deviation stdev of the motion detection data which are in particular acquired simultaneously or alternately to the motion quantification data. In particular the mean value m and/or the standard deviation stdev might be calculated from the set of motion detection data acquired during said time interval. For example, the object motion threshold might be equal to (m+/−N·stdev), with N≥0. In particular, the parameter N might be determined experimentally by a user/operator of the medical imaging system or predefined in function of the medical imaging technique. Preferentially, one or several intervals of tolerance defined by [mi−Ni·stdevi; mi+Ni·stdevi] might be defined for one or several object motion characteristics $c_i$, wherein the object motion characteristic is for example a specific motion amplitude and/or speed and/or direction, and wherein i>0 is the number of intervals of tolerance. For instance if during the diagnostic measurement, a motion characteristic $c_i$, for example a specific motion amplitude, is detected and its corresponding motion detection data belong to the interval of tolerance [mi−Ni·stdevi; mi+Ni·stdevi], then said motion characteristic $c_i$ is considered as not relevant since it stays within the tolerance interval.

ii. if said object has moved, in particular has moved during said time interval, then correlating the motion quantification data and the motion detection data, in particular taken simultaneously, or in immediate succession in the case of data acquired alternately and in particular during said time interval, for determining an object motion threshold for the motion detection system notably in function of a user-defined image quality of a diagnostic image (i.e. the final image used for diagnosis), wherein the threshold is determined from motion detection data correlated to motion quantification data characterizing an object motion that remains within a predefined tolerance value. In particular, threshold and tolerance interval in the case of a moving object are determined and calculated as previously described in step b(i). Preferentially, the present method comprises determining from the motion quantification data if an object motion will corrupt a diagnostic image or not, and defining the threshold of the motion detection system from motion detection data correlated to the motion quantification data that will not corrupt said diagnostic image. In particular, a motion quantification data is considered as corrupting a diagnostic image if it exceeds the predefined tolerance value. Said predefined tolerance value is for example determined from or is a value of a motion characteristic for which the diagnostic image will be corrupted if said value of the motion characteristic is exceeded. For example, an object displacement with a motion amplitude higher than a predefined tolerance value of a fraction of a pixel considered as impeding the resulting quality of the diagnostic image data, e.g. based on the rational described in the document MacLaren J. et al., Magnetic Resonance Imaging 2010. Typically, 0.5 pixels might be considered as relevant. Then, the correlation according to the invention between motion quantification data and motion detection data allows to determine which motion detection data correspond to said object displacement, and consequently, to determine a threshold for said motion detection system. Optionally, the calibration process according to the invention proposes to use the motion quantification data for extracting a subset of data from the motion detection data, wherein said subset of data comprises only motion detection data acquired for identical object positions, and then, applying step (i) to said subset of data.

Preferentially, object displacements/motions are then analyzed during the diagnostic measurements of said object being in the position and place allowing its imaging by said medical imaging system, e.g. placed inside the static magnetic field of the MRI scanner, according to the following steps:

c. using said motion detection technique for detecting object motion, wherein each motion detection measurement is separated from the next motion detection measurement by a temporal interval, each motion detection measurement enabling the acquisition of a set of motion detection data during the diagnostic measurements, the time at which is acquired one of said sets of motion detection data being therefore temporally separated from another directly successive set of motion detection data by said temporal interval;

d. for each motion detection data of the set of motion detection data, determining if the motion detection data exceeds the threshold or not, notably by comparing the acquired object motion data to the threshold, and if the threshold is exceeded, then activating a method configured for improving the diagnostic image, such a method preferentially comprising performing at least one of the following steps:

(I) triggering a quantification measurement for acquiring new motion quantification data and using said new motion quantification data for improving the image quality; or (II) performing prospective correction (i.e. applying changes to the following acquisitions); or (III) performing retrospective correction (i.e. applying modifications to the acquired data; or (IV) performing a re-acquisition technique (i.e. re-acquiring selected readouts); or (V) performing a combination of the steps (I)-(IV), for example step (I) followed by step (II) or (III).

Optionally, motion detection data are continuously acquired during diagnostic measurements, and a temporal information indicating at which time motion detection data exceeded the threshold or were outside of the interval of tolerance is recorded and/or processed for notifying an operator/user of the medical imaging system that object motion occurred. Advantageously, the operator/user will thus receive, according to the present invention, live information regarding the object motion.

Advantageously, the present invention combines a fast motion detection technique and a precise motion quantification technique for automatically setting the threshold between "relevant" and "irrelevant" object motion for the motion detection technique. The whole calibration process according to the invention might take place automatically. During the automatic calibration of the motion detection system, input might be automatically required from the medical imaging system user/operator in order to define e.g. the user-defined image quality, or might be predefined in a database of the medical imaging system, for instance in function of different image qualities In particular, the motion detection system, as well as the motion quantification system, can each comprise a dedicated device, e.g. a motion detection device and respectively a motion quantification device specifically designed for detecting motion and respectively quantifying motion, or may utilize imaging modalities used for imaging the object, or a combination of the use of signal acquisition or imaging modalities and dedicated device(s). In particular, examples of dedicated devices are the camera system, the respiratory belt, etc., and examples of signal acquisition or imaging modalities are FID-navigator, pencil-beam-navigator, or for instance MR-based methods, or from a general point of view, methods based on interpreting raw signals of the particular modality.

According to the present invention, a calibration of the motion detection system takes place preferentially before the start of the diagnostic measurements by means of the medical imaging system. For this purpose, data are repeatedly acquired according to the motion detection technique and the motion quantification technique without requiring specific object displacements. In other words, the pro-posed calibration does not require a specific participation of a patient for the de-termination the threshold(s). For example, in the case of MR imaging, motion detection data and motion quantification data for determining said threshold might be acquired during a dedicated time preceding or integrated into the diagnostic measurements and while the patient is inside the static magnetic field of the MRI scanner, in a manner free of any specific motion instructions provided to the patient for the determination of said threshold. In particular, the motion detection data and the motion quantification data might be taken alternatingly or at the same time. Also, a calibration according to the present invention might take place during diagnostic measurement, either in combination with or without any acquisition of motion detection data and motion quantification data before the start of the diagnostic measurements. In this case, no decision regarding "relevant" or "irrelevant" object motion will take place during the diagnostic measurement until a threshold is defined.

Preferentially, and as an improvement, the calibration process is automatically stopped after a duration T and the diagnostic measurements begins automatically after said duration T. Preferentially, the duration T is for example a function of the standard error or a mean value of the motion detection data, notably for a motion characteristic, e.g. motion amplitude of the head. For example, motion detection data and motion quantification data might be permanently analyzed according to the previously described calibration process until the standard error or a mean value of the motion detection data reaches a predefined value for a motion characteristic. Once said predefined value is reached, the calibration process stops. Therefore, said duration T is in particular the time needed for reaching a predefined mean value or a predefined standard deviation for the motion detection data. Optionally, a maximum time period TM might be predefined for the duration T, so that when the duration T equals said maximum time period TM, then the calibration process automatically stops for allowing the diagnostic measurements to begin. Preferentially, the calibration process according to the invention comprises a recognition of non-cooperative patients. For this purpose, continuous irregular motion of the object might be determined by analyzing the motion quantification data. In particular, the determination of continuous irregular motion according to the present invention may trigger a sending of an alert signal to an operator of the medical imaging system, e.g. the MRI scanner, so that said operator may do the necessary for calming down the patient.

Preferentially, the present invention proposes also an acquisition of motion detection data and motion quantification data during the diagnostic measurements for continuously improving thresholds defined during the calibration process taking place before the diagnostic measurements, e.g. by calculating new mean values or new standard deviations for the motion detection data, notably for a motion characteristic. Said motion detection data and motion quantification data might be acquired according to the steps b(i) and b(ii) previously described.

Preferentially, the method according to the invention comprises memorizing in a memory calibration data obtained for each object for which a calibration process took place, and reusing said calibration data during a further diagnostic measurement of said object while using the same medical imaging system configuration, e.g. the same MRI scanner configuration, as used during the calibration process. The calibration data comprise for example the threshold(s) defined for said object in function of the medical imaging system configuration, motion detection data and/or motion quantification data that might be used for further processing, as well as their relation which is determined during the statistical analysis.

Other features which are considered as characteristic for the invention are set forth in the appended claims.

Although the invention is illustrated and described herein as embodied in a method for the automatic calibration of motion detection techniques in medical imaging systems it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

We will describe now a preferred embodiment of the present invention by taking the particular case of MRI for illustrating the present invention in more detail. It will be understood, however, that the present invention is not restricted to MRI and may apply to any suitable medical imaging technique. For example, according to the present invention, any combination of a motion detection and a motion quantification technique/system is claimed. Examples for MR-based and non-MR detection and quantification techniques have been previously described. Rapid imaging using 2D or 3D EPI will be taken as example for an MR-based quantification technique, but others techniques including k-space navigators (orbital, spherical, cloverleaf, . . . ), multi-slice or 3D MR images (gradient or spin echo, EPI), orthogonal MR images, etc., might be used.

The present invention proposes in particular to use the imaging modalities of a conventional MRI scanner for performing the calibration process. For example, if an MRI scanner enables a fast FID-Navigator for the motion detection and a precise EPI volume acquisition for the motion quantification, then those techniques might be used for the calibration process. In this particular case, the imaging system comprises devices for performing the FID-Navigator and for performing the EPI volume acquisition. In particular the medical imaging system according to the invention may comprise devices used for both FID-Navigator and EPI volume acquisition.

Figure 1:
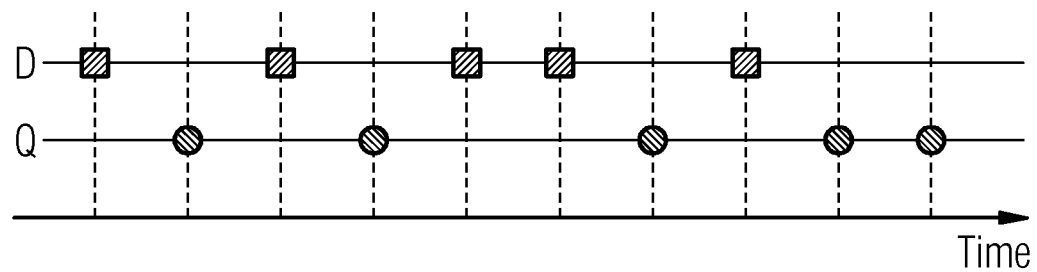
FIG. 1 is a graph schematically illustrating motion detection measurements and motion quantification measurements performed alternatingly during a calibration process according to the invention.
Figure 2:
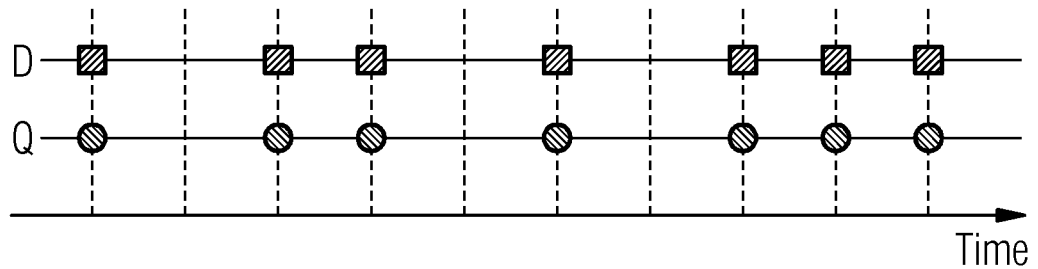
FIG. 2 is a similar graph illustrating motion detection measurements and motion quantification measurements being carried out simultaneously.

During the calibration process, measurements of motion detection D by means of the FID-Navigator and measurements of motion quantification Q by means of the EPI volume acquisition are carried out for acquiring respectively motion detection data and motion quantification data. Depending on the RF excitation pulse, motion detection measurements D and motion quantification measurements Q can be carried out either alternatingly or simultaneously by means of the MRI scanner as schematically illustrated by FIG. 1 and FIG. 2 respectively. The choice between simultaneous or alternate acquisition of motion detection data and motion quantification data may thus depend on the MRI pulse sequence chosen for imaging the object.

The first motion quantification measurement Q serves, in particular, as a reference. By supposing for example that the object motion is a motion of a rigid body (e.g. head examination) and by using a registration method (image registration refers to the alignment of two MRI images, so that common features overlap and differences between the two images are emphasized, making it possible to determine if a motion occurs between the acquisition of the respective images. In other words, image registration is capable of identifying the parameters of a transformation model (e.g. rigid body) that yield the best match between reference and (transformed) second image, wherein "best match" refers to a certain cost function (e.g. cross-correlation, mutual information, etc.). Such a registration method is well known to those of skill in the art and it does not need to be more described here. The present invention proposes notably to determine motion characteristics (e.g. three translation parameters and three rotation parameters) from the motion quantification measurements. In particular, the present invention proposes to create a database comprising said motion characteristics and to use said database for determining during the calibration process whether the object or patient moves or moved significantly, by using for example the registration method. If, for example, the object to be imaged is a joint (e.g. a knee), the detection will determine if the joint angles, and the quantification will determine to which degree the joint angles by using the method according to the invention.

If no relevant movement/motion of the object occurs during the calibration process, i.e. if no relevant movement/motion of the object is detected by the motion quantification measurements during the calibration process, then the method according to the invention comprises:

determining/selecting for each motion detection measurement one or several motion detection data that will be used for the calibration process. Said one or several motion detection data might be for instance the maximum/middle/integral/mean amplitude of the detection signal and/or the phase/mean phase of the detection signal at a certain time. In particular, a motion detection data might be a measure of the noise which is characteristic to the acquisition of the detection data. Advantageously, knowing the expected noise in the detection data, makes it possible to determine a threshold that will be high enough to not (or less likely) generate a false positive detection caused by measurement;

from said one or several motion detection data, calculating the mean value and/or the standard deviation of the motion detection data, notably for each motion characteristic of the object;

determining a threshold or tolerance interval for said motion detection data, notably for each motion characteristic of said object. For example, a threshold or a tolerance interval for a motion characteristic might be determined by using the calculated mean average value and/or the standard deviation of the motion detection data. In particular, for each motion characteristic, a tolerance interval for the motion detection data might be defined, wherein said tolerance interval is given by [mean value−2*standard deviation; mean value+ 2*standard deviation].

If a relevant movement/motion of the object occurs during the calibration process, then the method according to the invention comprises:

determining/selecting for each motion detection measurement one or several motion detection data that will be used for the calibration process. Said one or several motion detection data might be for instance the maximum or middle amplitude and/or the phase of the navigator signal;

determining a correlation between said one or several motion detection data and one or several motion quantification data so that the motion detection data and their correlated motion quantification characterize the same object motion, and optionally determining a motion characteristics of said same object motion;

determining a set of said one or several motion detection data having the highest correlation with the object motion quantification, preferentially said determination of the highest correlation being done for each motion characteristic;

determining a threshold or tolerance interval of the motion detection data, of the set of motion detection data characterized by said high correlation, and notably for each motion characteristic so that said motion characteristic, e.g. a motion amplitude, will be considered as irrelevant only if it belongs to the tolerance interval defined for said motion amplitude.

According to the present invention, diagnostic measurements for the same object as analyzed during the calibration process might be performed with the same medical imaging system used for said calibration process directly after the calibration process, or later on, since information regarding said threshold/tolerance interval might be in the latter case memorized in a database. During said diagnostic measurements, motion detection measurements are preferentially performed at time intervals that might be predefined, and motion detection data acquired and processed for being compared to the threshold/tolerance interval defined during the calibration process.

If the threshold is exceeded or if the processed motion detection data do not fall within the tolerance interval, then a) the acquisition of diagnostic data is temporarily interrupted and a motion quantification measurement Q is started. Motion quantification data are acquired and might be used for example for correcting the coordinate system of the MRI scanner in order to take into account the object motion (prospective correction). After said correction of the coordinate system, the acquisition of diagnostic data might be automatically restarted from the point where it stopped. Alternatively or in addition, motion information arising from said motion quantification data might be used for correcting the acquired diagnostic data in order to improve the diagnostic images (retrospective correction).

b) or alternatively, corresponding diagnostic data acquired during an object motion for which the motion detection data fall outside the tolerance interval or exceed said threshold are market as corrupted and new diagnostic data are acquired for replacing the corrupted diagnostic data (re-acquisition). The re-acquisition can be carried out immediately after observing a motion for which motion detection data fall outside of the tolerance interval or exceed said threshold, or in a later step, e.g. at the end of the diagnostic measurement.

Preferentially, calibration data, i.e. thresholds, motion detection data and/or motion quantification data acquired during the diagnostic measurement might be saved in the database for improving the calibration process, for example by doing a new statistical analysis of the motion detection data in order to determine an improved threshold or tolerance interval.

Finally, the present invention concerns also a medical imaging system working according to a medical imaging technique for imaging an object, said medical imaging system comprising a motion detection system working according to a motion detection technique and a motion quantification system working according to a motion quantification technique in order to respectively detect and quantify the motion of said object, said medical imaging system being configured for automatically processing the calibration process previously described. In particular, the medical imaging system is a magnetic resonance imaging system, the motion quantification technique is a EPI acquisition and the motion detection technique is a FID-Navigator.

To summarize, the method according to the invention enables a fast detection of object motion in a clinical routine, wherein the motion detection technique is precisely calibrated for the object to be diagnosed and the configuration of the medical imaging system used for the diagnostic measurement.

The invention claimed is:

1. A computer-implemented method for calibrating a motion detection system configured to carry out a motion detection technique for detecting a motion of an object during medical imaging in a medical imaging system, the computer-implemented method comprising:

with an object placed in the medical imaging system in a position suitable for imaging by the imaging system, performing an automatic calibration process for determining at least one motion threshold for the object motion detection system;

the automatic calibration process including:

a. carrying out the motion detection technique with the motion detection system by repeatedly acquiring motion detection data enabling object motion detection and carrying out a motion quantification technique with a motion quantification system by repeatedly acquiring motion quantification data enabling object motion quantification;

b. analyzing the motion quantification data for determining whether or not the object was mobile or immobile; and i. if the object was immobile, using the motion detection data for determining an object motion threshold for the motion detection system, the object motion threshold being determined by statistical analysis of the motion detection data;

ii. if the object was mobile, correlating the motion quantification data with the motion detection data for determining an object motion threshold for the motion detection system, the object motion threshold being determined from the motion detection data correlated with the motion quantification data characterizing an object motion that remains within a predefined tolerance value; and analyzing the object motion during diagnostic measurements of the object, with the object being in the position for imaging with the medical imaging system, by carrying out the following steps:

c. using the motion detection technique for detecting object motion, wherein each motion detection measurement is separated from the next motion detection measurement by a temporal interval, each motion detection measurement enabling an acquisition of a set of motion detection data during the diagnostic measurements; and d. for each motion detection data of the set of motion detection data, determining whether or not the motion detection data exceeds the threshold and, if the threshold is exceeded, activating a method configured for improving the diagnostic image.

2. The computer-implemented method according to claim 1, which comprises carrying out the calibration process before starting a diagnostic measurement.

3. The computer-implemented method according to claim 1, which comprises acquiring the motion detection data and the motion quantification data simultaneously or in alternation.

4. The computer-implemented method according to claim 1, which comprises determining the object motion threshold by calculating a mean value m and/or a standard deviation stdev of the motion detection data.

5. The computer-implemented method according to claim 4, wherein the object motion threshold is equal to m+/−N·stdev, with N≥0.

6. The computer-implemented method according to claim 1, which comprises setting the predefined tolerance value to a specific number of pixels.

7. The computer-implemented method according to claim 1, which comprises, if the object was mobile, using the motion quantification data for extracting a subset of data from the motion detection data, wherein the subset of data includes only motion detection data acquired for identical object positions, and applying step b(i) to the subset of data.

8. The computer-implemented method according to claim 1, comprising continuously acquiring motion detection data during diagnostic measurements and recording and processing temporal information indicating at which time the motion detection data exceeded the threshold, and notifying an operator of the medical imaging system about the occurrence of object motion.

9. The computer-implemented method according to claim 1, which comprises acquiring motion detection data and motion quantification data during the diagnostic measurements for continuously improving the threshold.

10. The computer-implemented method according to claim 1, which comprises automatically stopping the calibration process after a time duration T and automatically starting the diagnostic measurements following the time duration T.

11. The computer-implemented method according to claim 1, wherein the medical imaging system is a magnetic resonance imaging system, the motion quantification technique is a rapid gradient-echo-based acquisition, and the motion detection technique is a free induction decay (FID) Navigator.

12. A medical imaging system for imaging an object, the medical imaging system comprising:
  a motion detection system configured to operate according to a motion detection technique;
  a motion quantification system configured to operate according to a motion quantification technique;
  said motion detection system and said motion quantification system respectively detecting and quantifying motion of the object; and
  wherein the medical imaging system is configured for automatically processing the calibration process of the motion detection system according to claim 1.

13. The medical imaging system according to claim 12, wherein said medical imaging system is a magnetic resonance imaging system, the motion quantification technique is a rapid gradient-echo-based acquisition and the motion detection technique being a free induction decay (FID) Navigator.

* * * * *